US012629545B2

(12) United States Patent
Melo De Lima et al.

(10) Patent No.: US 12,629,545 B2
(45) Date of Patent: May 19, 2026

(54) THERAPEUTIC ULTRASONIC TRANSDUCERS FOR THE EMISSION OF FOCUSED ULTRASOUND WAVES

(71) Applicants: INSTITUT NATIONAL DE LA SANTE ET DE LA RECHERCHE MEDICALE (INSERM), Paris (FR); Université Claude Bernard Lyon 1, Villeurbanne (FR); CENTRE LEON BERARD, Lyons (FR)

(72) Inventors: David Melo De Lima, Lyons (FR); Sophie Cambronero, Lyons (FR)

(73) Assignees: INSTITUT NATIONAL DE LA SANTE ET DE LA RECHERCHE MEDICALE (INSERM), Paris (FR); Université Claude Bernard Lyon 1, Villeurbanne (FR); CENTRE LEON BERARD, Lyons (FR)

( * ) Notice: Subject to any disclaimer, the term of this patent is extended or adjusted under 35 U.S.C. 154(b) by 0 days.

(21) Appl. No.: 18/547,720

(22) PCT Filed: Feb. 25, 2022

(86) PCT No.: PCT/EP2022/054753
§ 371 (c)(1),
(2) Date: Aug. 24, 2023

(87) PCT Pub. No.: WO2022/180198
PCT Pub. Date: Sep. 1, 2022

(65) Prior Publication Data
US 2024/0139554 A1      May 2, 2024

(30) Foreign Application Priority Data
Feb. 26, 2021 (EP) ..................................... 21305235

(51) Int. Cl.
A61N 7/02          (2006.01)
A61N 7/00          (2006.01)

(52) U.S. Cl.
CPC ........ *A61N 7/02* (2013.01); *A61N 2007/0065* (2013.01); *A61N 2007/0078* (2013.01); *A61N 2007/027* (2013.01)

(58) Field of Classification Search
CPC .............. A61N 7/02; A61N 2007/0065; A61N 2007/0078; A61N 2007/027;
(Continued)

(56) References Cited

U.S. PATENT DOCUMENTS

2009/0230823 A1* 9/2009 Kushculey ............... A61N 7/02
310/366
2009/0281463 A1 11/2009 Chapelon
(Continued)

FOREIGN PATENT DOCUMENTS

EP        3888748 A1    10/2021
IL          102516 A     1/1996
(Continued)

OTHER PUBLICATIONS

Vincenot Jeremy et al., "Electronic Beam Steering Used with a Toroidal HIFU Transducer Substantially Increases the Coagulated Volume", Ultrasound in Medicine and Biology., vol. 39, No. 7, Jul. 1, 2013 (Jul. 1, 2013), p. 1241-1254.

*Primary Examiner* — Serkan Akar
(74) *Attorney, Agent, or Firm* — WCF IP

(57) ABSTRACT
The disclosure relates to ultrasonic transducers for therapeutic ultrasound techniques, such as high-intensity focused ultrasound (HIFU) techniques. A challenge is to design ultrasound transducers capable of delivering the required pressure, deep enough in the biological tissue, and with enough precision to deliver the required pressure within the
(Continued)

targeted volume of the tissue and without destroying the surrounding tissue. Thus, it is proposed to use a transducer with several ultrasound emitting zones capable of being activated independently. This enables the transducer to deliver the required pressure at a target location that is not aligned with the emission axis.

17 Claims, 6 Drawing Sheets

(58) Field of Classification Search
CPC .......... A61N 2007/0095; B06B 1/0215; B06B 2201/20; B06B 1/0622; B06B 2201/76; G10K 11/32
See application file for complete search history.

(56) References Cited

U.S. PATENT DOCUMENTS

| | | | |
|---|---|---|---|
| 2014/0081300 A1* | 3/2014 | Melodelima ............. | A61N 7/02 |
| | | | 606/169 |
| 2018/0360420 A1 | 12/2018 | Vortman et al. | |
| 2020/0037990 A1* | 2/2020 | Qiao ........................ | A61N 7/00 |
| 2020/0391245 A1* | 12/2020 | Barrett ................... | H10N 30/06 |

FOREIGN PATENT DOCUMENTS

| JP | 2012517868 A | 8/2012 | |
|---|---|---|---|
| WO | 1998007373 A1 | 2/1998 | |
| WO | WO-2010094349 A1 * | 8/2010 | ............. A61F 9/00 |
| WO | 2012094850 A1 | 7/2012 | |
| WO | WO-2012131213 A1 * | 10/2012 | ..... A61B 17/320068 |
| WO | 2017089511 A1 | 6/2017 | |
| WO | 2020203317 A1 | 10/2020 | |

* cited by examiner

FIG.3

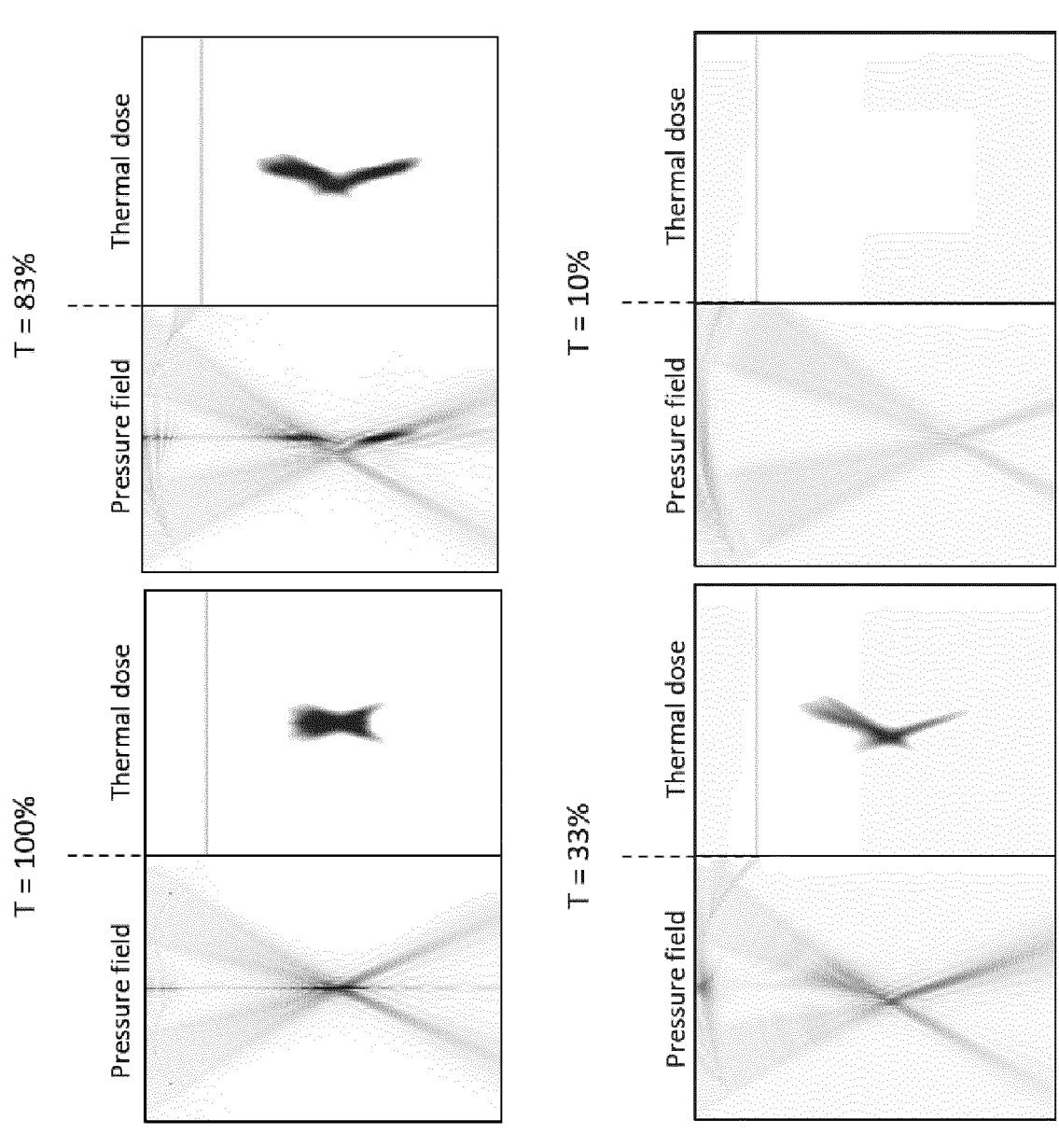
_FIG.4_

THERAPEUTIC ULTRASONIC TRANSDUCERS FOR THE EMISSION OF FOCUSED ULTRASOUND WAVES

TECHNICAL FIELD

The present disclosure relates to ultrasonic transducers.

BACKGROUND

Therapeutic ultrasound techniques, such as high-intensity focused ultrasound (HIFU) techniques, are increasingly used in a wide range of applications as a non-invasive method for destroying targets, such as tumors, in biological tissues or organisms.

Generally, one or more ultrasonic transducers are used to generate an ultrasound beam directed to a target located inside a biological tissue or organism. The ultrasound beam generates waves of mechanical pressure at specific locations inside the biological tissue, which result in a local increase of temperature, leading to the destruction of the target.

A challenge is to design ultrasound transducers capable of delivering the required pressure, deep enough in the biological tissue, and with enough precision so as to be able to deliver the required pressure within the targeted volume of the tissue and without destroying the surrounding tissue.

It has been proposed to use an ultrasound probe comprising a concave shaped curved emission surface, the emission surface being toroidal and divided into two sectors having different focusing properties.

A drawback of this approach is that, while satisfactory for some applications, most of the pressure is still delivered along the emission axis of the transducer. Thus, the transducer cannot deliver the maximum pressure at a target location that is not aligned with the emission axis (or acoustic axis). This means that, in some cases, the transducer has to be physically moved. The ultrasound beam may then have to be refocused, which is time consuming and prone to errors. In some cases, it may not be possible to position the transducer so that the emission axis is aligned with the target location.

In addition, treating an area of tissue with complex patterns deviating from the acoustic axis presents challenges. Indeed, treatment with focused ultrasonic waves, in the broad sense of the term, of a complex configuration requires a large number of elements (and therefore associated electronics) and a long processing time. In the case of treatment with ultrasonic waves focused by a toroidal transducer, the pressure remains maximum along the acoustic axis, which implies a difficulty in widening the treatment area with respect to the acoustic axis and in treating complex configurations that do not have a symmetry of revolution.

There is therefore a need for ultrasonic transducers capable of overcoming at least some of the aforementioned drawbacks.

SUMMARY

An object of the present invention is therefore to provide an ultrasonic transducer comprising a base portion and a plurality of ultrasound emitter elements located on a surface of the base portion, the base portion displaying a rotational symmetry relative to the emission axis of the transducer, wherein said surface is divided in several ultrasound emitting zones, wherein at least one of the ultrasound emitting zones, named first central ultrasound emission zone, has a rectilinear shape and is arranged centrally on said surface.

The surface of the central ultrasound emission zone(s) is comprised between 25% and 50% of the total surface of the base portion.

Such an approach makes it possible to maximize the pressure at a distance from the acoustic axis by minimizing the pressure on the axis and therefore to have an optimal treatment of the targeted area, by minimizing the risk of secondary lesions along the acoustic axis. This optimization is linked to the ratio between the rectilinear surface and the total surface of the transducer.

According to advantageous optional aspects, alternative embodiments of the invention may comprise one or more of the following features, taken alone or according to all possible technical combinations:

a second of the ultrasound emitting zones of the ultrasonic transducer has a rectilinear shape and is arranged centrally on said surface, the first and the second central ultrasound emission zones being arranged relative to each other to form a cross shape.

a second of the ultrasound emitting zones of the ultrasonic transducer has a rectilinear shape and is arranged centrally on said surface, the first and the second central ultrasound emission zones being arranged so as to cross each other with any angle between the first and second central ultrasound zones.

Each of the two central ultrasound emitting zones can be divided into two parts that can be activated independently.

the ultrasonic transducer is configured so that the first and the second central ultrasound emission zones can be activated independently from each other.

the ultrasonic transducer is configured so that the other ultrasound emission zones of the ultrasonic transducer can be activated independently from the central ultrasound emission zone(s).

the ultrasonic transducer is configured so that each ultrasound emission zones of the ultrasonic transducer can be activated independently from the other ultrasound emission zones.

The base portion has a diameter comprised between 10 mm and 300 mm, and is preferably comprised between 90 mm and 130 mm.

the surface of the central ultrasound emission zone(s) is comprised between 25% and 50% and ideally equal to 33% of the total surface of the base portion.

the base portion has a concave shape and preferentially a frustoconical shape or a toroidal shape.

the ultrasonic transducer is a high intensity focused ultrasound (HIFU) transducer.

the ultrasonic transducer comprises a layer of piezoelectric material and at least one electrically conductive electrode layer arranged in contact with the layer of piezoelectric material, wherein the electrode layer is divided in a plurality of contact pads, the association of each contact pad with the piezoelectric layer forming an ultrasound emitter element, wherein each emission zone of the electronic transducer comprises one or more of said contact pads.

According to another aspect, the invention relates to a device comprising an ultrasonic transducer and a control unit connected to the ultrasonic transducer, wherein the ultrasonic transducer is according to any one of the previous claims, and wherein said control unit comprises at least one signal generator for driving the ultrasound emitter elements, preferably with a matching circuit between the generator and the ultrasound emitter elements.

According to another aspect, the control unit is configured to activate each ultrasound emission zone of the ultrasonic transducer independently from the other ultrasound emission zones.

According to another aspect, the device is a therapeutic ultrasonic device configured to generate at least one focused ultrasound beam.

According to another aspect, the invention relates to a therapeutic method using the device described above on a human patient.

BRIEF DESCRIPTION OF THE DRAWINGS

The invention will be understood upon reading the following description, provided solely as an example, and made in reference to the appended drawings, in which:

FIG. 3 illustrates a graph displaying a comparison of the relative gain in the pressure delivered by several ultrasonic transducers, as a function of the ratio between the surface of one of the rectilinear emitting zone and the total surface of said transducer.

FIG. 4 illustrates a comparison of the pressure field and the corresponding thermal dose delivered by several exemplary ultrasonic transducers FIG. 5 schematically illustrates the ultrasound transducer of FIG. 1 represented in three-dimensional views.

DESCRIPTION OF SOME EMBODIMENTS

Figure 1:
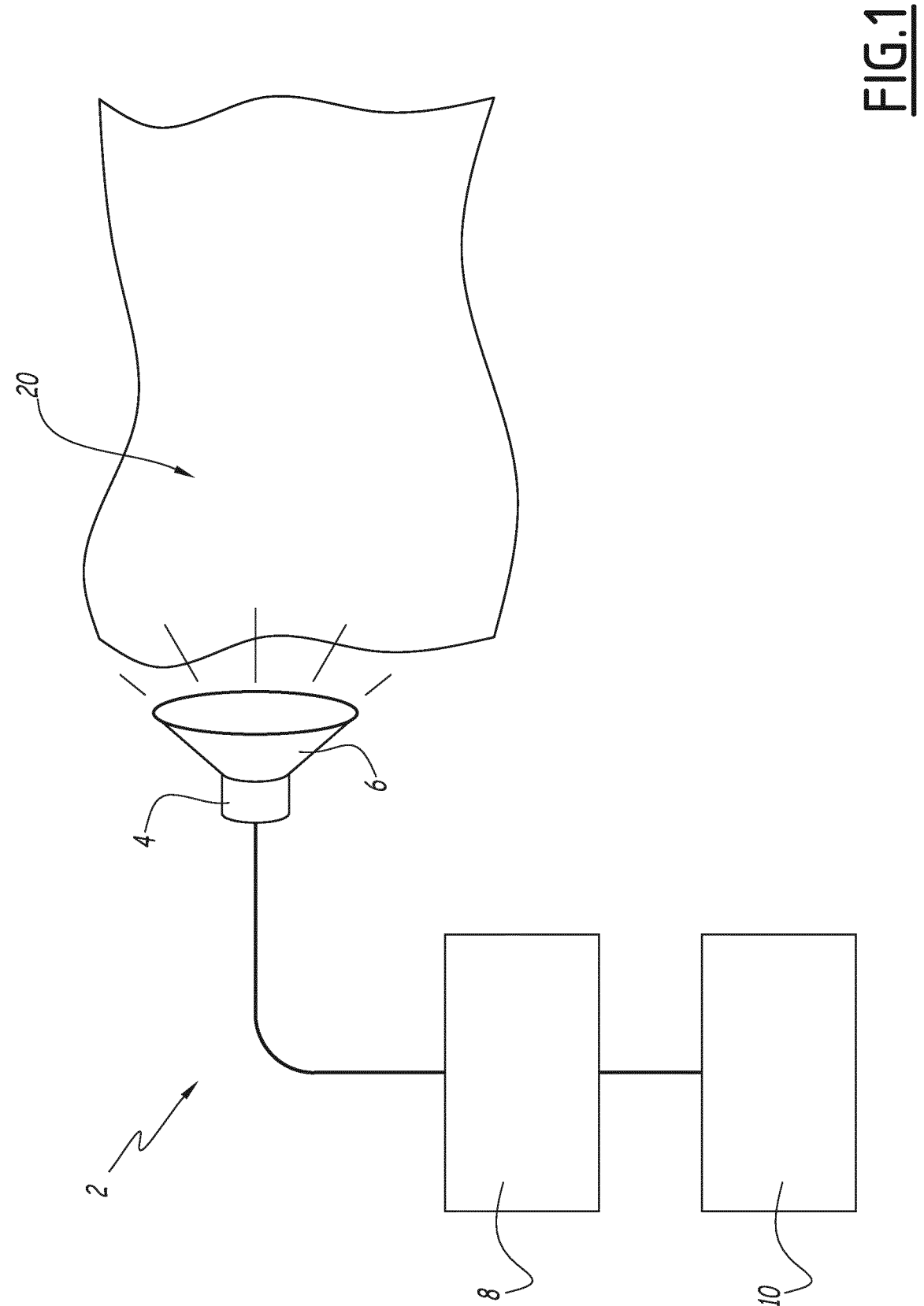
FIG. 1 is a schematic diagram of an ultrasound system comprising an ultrasound transducer according to embodiments of the invention.

On FIG. 1 there is illustrated an embodiment of an ultrasound device 2 comprising an ultrasound emitting device 4 comprising one ultrasonic transducer 6.

In the illustrated example, the ultrasound device 2 also comprises a control unit 8 and a user control interface 10.

The control unit 8 comprises suitable electronic circuitry for performing various operations in support of its functions. For example, the control unit 8 may comprise a generic processor, such as a microprocessor or a microcontroller, or a specific purpose processor such as a digital signal processor (DSP) or a graphical processor unit (GPU), or as an application-specific integrated circuit (ASIC), or in a field-programmable gate array (FPGA). In addition, analog circuits can be used to execute many of the same functions.

In many embodiments, the control unit 8 comprises at least one signal generator for driving ultrasound emitter elements of the ultrasonic transducer 6, as will be explained later.

In practice, the control unit 8 is connected to the transducer 6 by means of one or more electrical connectors, such as cables.

The user control interface 10 may comprise a human machine interface such as a display screen and/or data input means such as a keyboard, or a touch sensitive screen, or a pointer, or any equivalent device, or any combination thereof.

The ultrasound device 2 is configured to deliver ultrasonic waves, for example to destroy a target in a host material 20, such as a biological tissue.

For example, the ultrasound device 2 is configured to generate at least one focused ultrasound beam directed to a target region of the host material 20.

This generates mechanical vibrations in the host material 20 and creates in turn a controlled local increase in temperature within the host material 20, which may be used to destroy a target, such as a tumor. This is referred to as a "thermal dose" in what follows.

In some embodiments, the host material 20 may not necessarily be a biological tissue and may be, for example, a soft material, such as a food idem or a gel.

The ultrasound device 2 may be a medical or therapeutic device.

For example, the ultrasonic transducer 6 is a high intensity focused ultrasound (HIFU) transducer.

In many embodiments, the ultrasound emitting device 4 comprises a casing enclosing the ultrasonic transducer 6 and may also comprise a connector for connecting the transducer 6 to a cable connected to the control unit 8. In addition, a matching circuit (such as an impedance matching circuit) may be used between the transducer 6 and the control unit 8 to transmit the electric signal to the transducer 6 with minimal electrical losses.

In the illustrated embodiment, the control unit 8 is shown to be a device separate from the ultrasound device 4. However, in some embodiments, the control unit 8 may be placed inside the casing of the device 4.

In some embodiments, the control unit 8 may be combined with the interface 10 into a single device.

Figure 2:
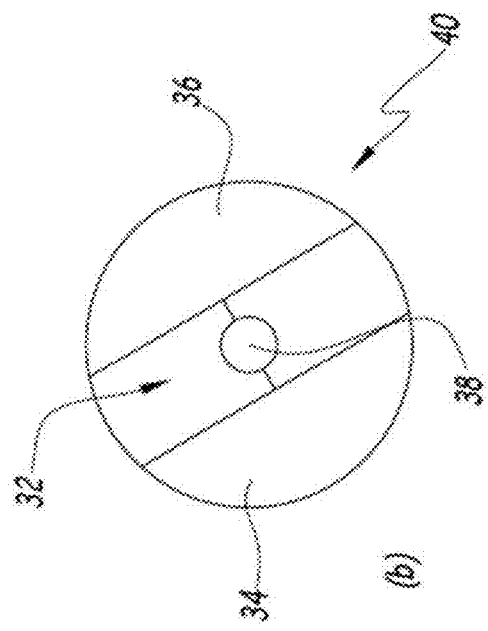
FIG. 2 illustrates several embodiments of the ultrasound transducer of FIG. 1.
Figure 2:
Figure 2:
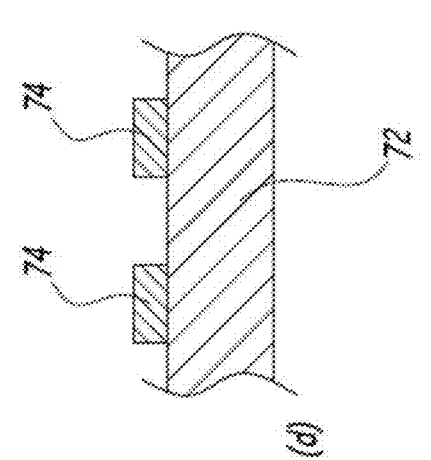
Figure 2:
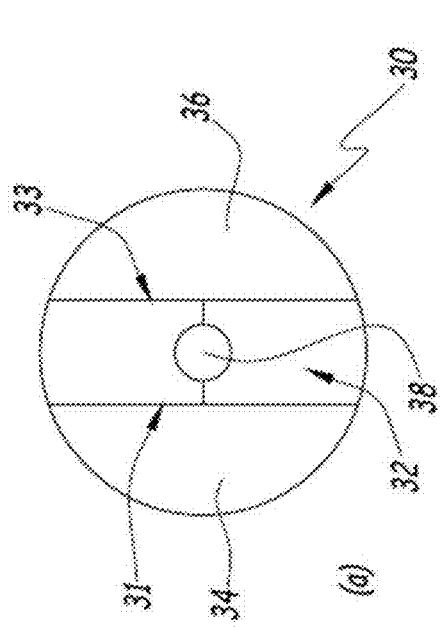
Figure 2:
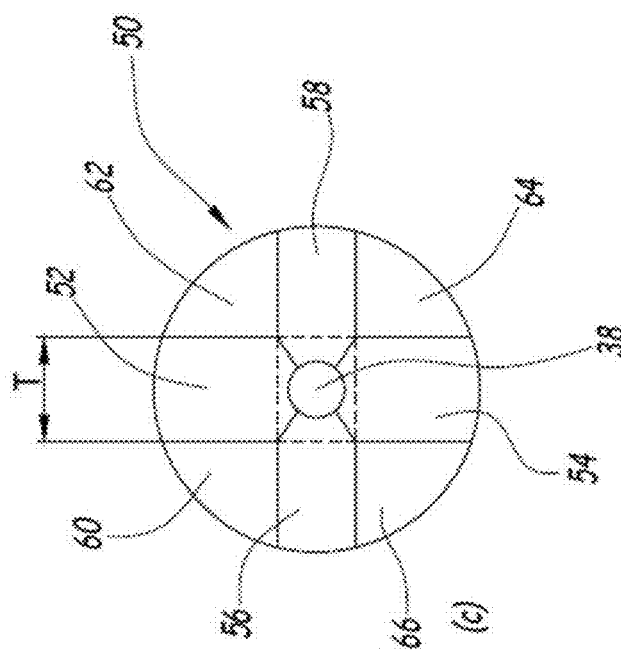

Embodiments of the ultrasonic transducer 6 are illustrated on FIG. 2.

In most embodiments, the ultrasonic transducer comprises a base portion and a plurality of ultrasound emitter elements located on a surface (so-called "emitting surface") of the base portion. In this example, the base portion has a circular shape.

Preferably, the base portion has a concave shape centered on an emission axis of the transducer 6.

For example, the base portion may have a frustoconical shape (such as a truncated cone), or a toroidal shape (such as a truncated torus), a conical shape or a bell-like shape or a bent disk shape. The base portion may be shaped so as to display a rotational symmetry relative to the emission axis. In other words, the base portion displays a rotational symmetry relative to the emission axis of the transducer.

An example of the concave shape of the base portion can be found, for example, in the published European patent EP 2 035 091 B1. In that case, the base portion has a truncated toroidal shape (more precisely, the base portion is built on a portion of the interior envelope of a spindle torus). A torus can be built mathematically by rotating a circle around a rotation axis, said circle being laterally offset from the rotation axis (i.e. offset in a direction perpendicular to the rotation axis). If the distance between the rotation axis and the center of the circle is lower than the radius of the circle, the torus is a spindle torus. The rotation axis corresponds to the emission axis of the transducer. Examples of construction rules for a truncated toroidal shape built on a portion of the interior envelope of a spindle torus can be found in the journal article Melodelima et al., Applied Physics Letters 2009; 91(19):193901.

This example is not limiting and other shapes are possible.

For example, the diameter of the transducer 6 may be comprised between 1 cm and 30 cm, preferably equal to 12 cm. This example is not limiting.

According to preferred embodiments, the surface is divided in several ultrasound emission zones (or emission regions). For example, the ultrasound emitting zones comprise portions of piezoelectric material capable of emitting ultrasound waves independently from other regions of the transducer 6.

At least one of the ultrasound emitting zones, named first central ultrasound emission zone, has a rectilinear shape and is arranged centrally on said surface. The rectilinear shape may be a rectangle shape, or an elongated strip shape. Thus, the ultrasound emitting zones may be band-shaped.

Figure 5:
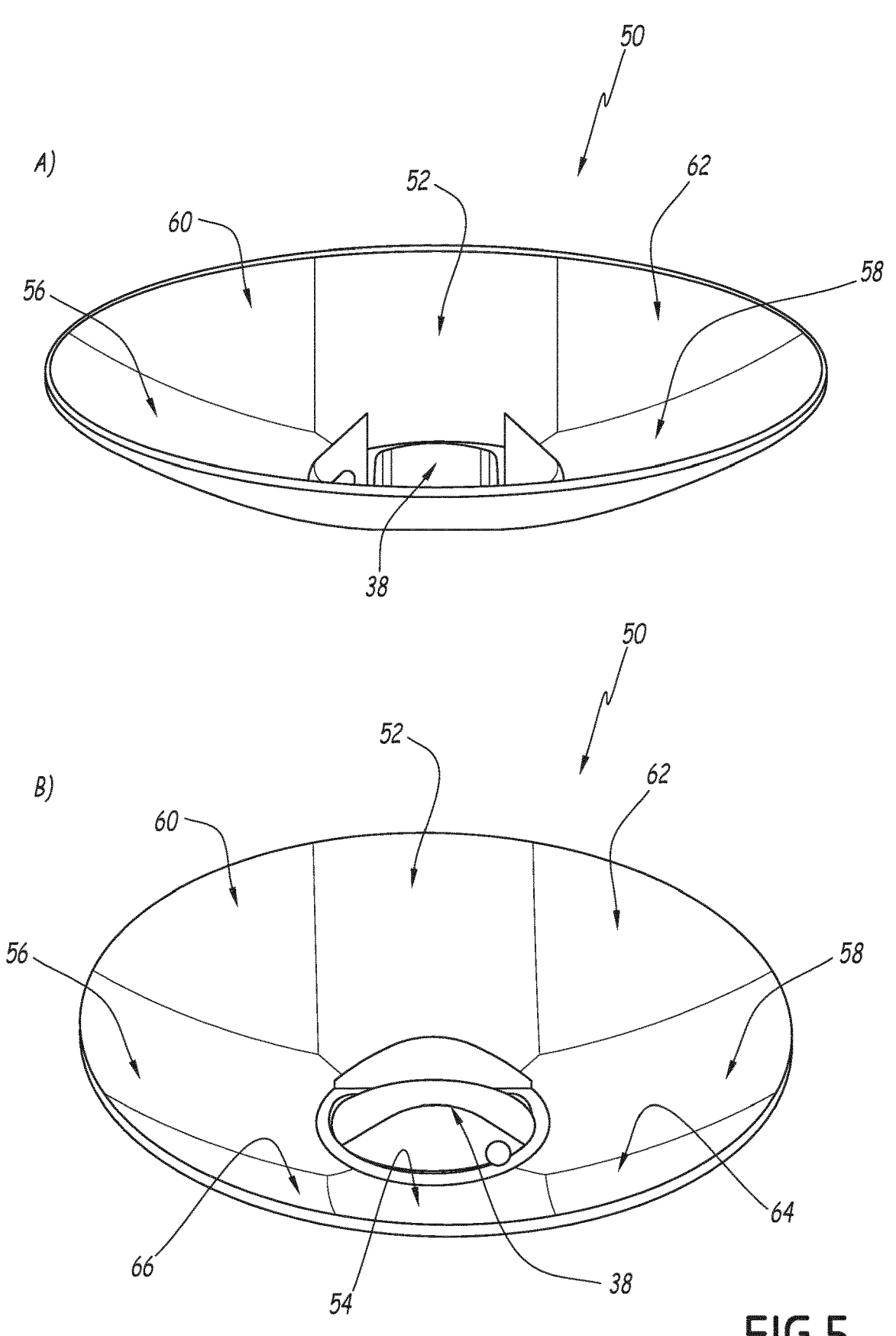

Preferably, the or each rectilinear ultrasound emitting zones (e.g., the band) is distributed on both sides of the emission axis of the transducer, the emission axis being arranged in a central position of the transducer (e.g., in a central position of the base portion, as in FIGS. 2 and 5).

In some embodiments, as illustrated in FIGS. 2 and 5, the or each band or rectilinear shape forming the central ultrasound emission zone(s) is wider than the central orifice 38.

In some other embodiments, the or each band or rectilinear shape forming the central ultrasound emission zone(s) can be narrower than the central orifice 38.

This emitting zone can be advantageously divided into two parts, preferably into two equal parts.

FIG. 2 illustrates several possible embodiments of the ultrasonic transducer 6.

In FIG. 2, the exemplary transducers 6 are illustrated in a two-dimensional view, corresponding to an elevated view from above. FIG. 5 represents two illustrations (insets A and B) of an example of a transducer 6 viewed in an isometric perspective (i.e., a three-dimensional view).

It is therefore understood that the transducers 6 are three-dimensional objects and that it is only for convenience and explanatory purposes that the transducers 6 appear in two dimensions on FIG. 2.

In the first example, visible on inset (a) of the FIG. 2, the ultrasonic transducer 30 comprises a central ultrasound emission zone, divided into two equal parts, in the shape of a strip 32.

For example, the ultrasonic transducer 30 also comprises other emission zones 34, 36, separated from the central zone 32 by parallel rectilinear cutout lines 31 and 33.

In many embodiments, the transducer comprises a central orifice 38, which may be used to insert an ultrasound imaging probe, or a camera, or any measurement device.

In the second example, visible on inset (b) of the FIG. 2, the ultrasonic transducer 40 comprises a central ultrasound emission zone 32 which is rotated relative to a vertical direction and is otherwise identical or similar to the transducer 30 described above.

In the third example, visible on inset (c) of the FIG. 2 and on FIG. 5, in the ultrasonic transducer 50, a second of the ultrasound emitting zones has a rectilinear shape and is arranged centrally on said surface.

For example, "centrally arranged" means that the rectilinear ultrasound emitting zones are distributed on both sides of the emission axis of the transducer, the emission axis being arranged in a central position of the transducer (e.g., in a central position of the base portion).

In addition, the first and the second central ultrasound emission zones (52+54, 56+58) being arranged relative to each other to form a cross shape. In other words, the first and second zones are arranged perpendicular to each other. This transducer 50 is otherwise identical or similar to the transducer 30 described above.

Preferably, the first and second zones extend across the entire diameter of the base portion, e.g. from one edge of the base portion to the opposite edge. Thus, in many embodiments, the first and second zones have the appearance of a cross inscribed within a circle or a disk.

In other embodiments, the first and the second central ultrasound emission zones are arranged so as to cross each other with any angle (i.e., the first and second zones are not necessarily arranged perpendicular to each other).

Preferably, the first and second central ultrasound emission zones cross each other at their respective geometrical centers.

In the illustrated example, each of the first and second zones is divided into two subzones (respectively 52, 54 and 56, 58), although this is not necessary and in other embodiments, each of the first and second zone could extend continuously as in the transducer 30 or 40 described above, or if the central orifice 38 was to be removed.

More precisely, in this example, the transducer 50 is divided into eight sectors: two of these sectors forming the first central zone, two other sectors forming the second central zone, and each of the remaining sectors forming one of the remaining zones 60, 62, 64 and 66.

In practice, as shown by the inset (d) of FIG. 2, schematically representing a cutout view of an exemplary transducer 6, the ultrasonic transducer 6 may comprise a layer of piezoelectric material 72 and at least one electrically conductive electrode layer arranged in contact with the layer of piezoelectric material.

The electrode layer is divided in a plurality of electrically conductive contact pads 74, for example by etching or by cutting the electrode layer with a mechanical saw, or by any appropriate means.

An ultrasound emitter element as defined previously is thus formed by the association of a contact pad 74 with the piezoelectric layer 72. The corresponding region of the piezoelectric layer 72 can be made to vibrate by applying a suitable electrical signal through the contact pad 74. Each emission zone 32, 34, 36; 52, 54, 56, 58, 60, 62, 64, 66 of the electronic transducer comprises one or more of said contact pads 74.

In the illustrated example, only one face of the piezoelectric material layer 72 is shown to be covered by an electrically conductive electrode layer. However, in practice, the electrically conductive electrode layer can be arranged on both the top and bottom faces of the piezoelectric layer 72, and electrically conductive contact pads 74 can be formed on each of said electrically conductive electrode layers.

Preferably, the ultrasonic transducer 6 is configured so that the first and the second central ultrasound emission zones 52+54 and 56+58 can be activated independently from each other.

In some further embodiments, the ultrasonic transducer 6 is configured so that the other ultrasound emission zones 60, 62, 64, 66 of the ultrasonic transducer can be activated independently from the central ultrasound emission zone(s).

In still some further embodiments, the ultrasonic transducer 6 is configured so that each ultrasound emission zone 32, 34, 36; 52, 54, 56, 58, 60, 62, 64, 66 can be activated independently from the other ultrasound emission zones.

For example, the zones 60, 62, 64 and 66 can be activated independently from each other and from the central zones 52/54 and 56/58. In some embodiments, the zones 60, 62, and 66 may remain deactivated, that is, they do not emit ultrasound waves.

In some embodiments, the zones may be controlled independently from each other by providing different control signals (excitation signals, i.e. electrical signals designed to force the piezoelectric material to vibrate at a given frequency with a specific amplitude and phase).

For example, each ultrasound emission zone 32, 34, 36 or 52/54, 56/58, and optionally 60, 62, 64, 66, is coupled to the control unit 8 to receive a control signal different from the control signal received from another emission zone.

For example, a first excitation signal is provided to the central zone 32, 52/54, so as to drive simultaneously all the emission elements of the zone. For example, the excitation signal is applied to all the electrical contact pads 74 located within said central zone.

Wherever applicable, a second excitation signal is provided to the second central zone 56/58, in a similar fashion.

One or more additional excitation signals may be provided to one or more of the other zones 60, 62, 64 and 66.

This, in preferred embodiments, the transducer 50 may be operated in at least three different activation modes: with only the first central emission zone activated, with both the first and the second central emission zones activated, and with all the emission zones 17 activated.

As previously explained, the control unit 8 comprises at least one signal generator for driving the ultrasound emitter elements, and preferably several signal generators.

In some embodiments, a signal generator may be associated to each zone. In some other embodiments, a signal generator may be used to drive several zones independently, with the aid of appropriate signal processing circuitry.

For example, in some embodiments, the control unit 8 comprises a multi-channel amplifier, such as a 32-channel amplifier, to create a plurality of control signals. The control unit 8 may also comprise a switching device for addressing said plurality of control signals to the corresponding In preferred embodiments, the surface of the central ultrasound emission zone(s) or 52/54, or 56/58, noted "T" on the inset (c) of FIG. 2, is comprised between 15% and 70% of the surface of the transducer (i.e. the surface of the base portion), and is preferably comprised between 25% and 50% of the surface of the base portion.

In preferred embodiments, the surface T of the central ultrasound emission zone(s) is comprised between 30% and 35% of the surface of the base portion and is most preferably equal to 33% of the surface of the base portion.

Preferentially, the surface T is equal to one third of the surface of the base portion.

The shape, dimensions and relative spatial arrangement of the central zone(s) 32, 52/54, 56/58 has been found to allow an increase of the amount of the thermal dose deposited in lateral directions relative to the emission axis. This is especially true when only the central zones (32, or 52/54, or 52/54 and 56/58 alternatively), are activated and the remainder of the transducer is not activated.

Preferably, the dimensions and the shapes of the first and second central zones 52/54 and 56/58 are similar or identical. However, in some embodiments, the first central zones 32, or 52 and 54, or 56 and 58, can have different widths.

And, in some embodiments, the first central zones 32, or 52 and 54, or 56 and 58, can have different lengths. For example, each first central zone can be partitioned in a plurality of slices that can be activated independently from the other slices of the central zone. Thus, it is possible to increase or decrease the activated length of each first central zone.

On FIG. 3, the graph 80 displays, as a function of the relative surface S (ratio between the surface T to the total surface of the base portion), the relative gain (expressed as a relative value) of deposited pressure along the emission axis (graph 82) compared to the deposited pressure in a region of the target material 20 distant from the emission axis (graph 84). In that example, only one of the central zones 52/54 and 56/58 of the transducer 50 were activated.

In this example, it can be seen that a surface T comprised between 15% and 70% of the surface of the transducer, and preferably comprised between 25% and 50% of the surface of the transducer maximizes the amount of off-axis pressure while minimizing the amount of pressure delivered along the emission axis.

Data points 90, 92 and 94 illustrate individual experimental measurements for two different transducer surfaces: 100% (ES mode) and 33% (Vertical mode). In all cases the focus was shifted 9 mm away from the acoustic axis. The experimental points 90, 92 and 94 show the absolute difference (which is between 2% and 15%) between the theoretical value (graphs 80 and 82) and the corresponding measured value.

For example, when defining the shape of the transducer, in the ES mode, the transducer is separated into two emitting equal surfaces (surface T=100%), by applying one radial slicing while shifting the treatment zone. The pressure is maximum on the axis and not at the treatment zone and as a result, the ablated zone is longer than broad. In the Vertical modes, radial slicing is applied so as to obtain a band (Vertical mode). As a result, the pressure reaches a maximum at the treatment zone and not on the emission axis while shifting the focalization.

On FIG. 4, there is illustrated a comparison of numerical simulation data showing four images of the magnitude and spatial distribution of the pressure field (leftmost part of each image) and of the delivered thermal dose (rightmost part of each image) in a region of the host material 20, for four different configurations of the transducer 50.

In the first configuration (top left of the figure), all the emission zones of the transducer are activated simultaneously. As a result, most of the thermal dose is delivered along the emission axis or close to the emission axis. The surface T of the central zones is equal to 100% of the surface of the transducer.

In the second configuration (top right of the figure), one of the central zones 52/54 or 56/58 of the transducer 50 are activated. The other zones are not activated and do not emit ultrasound waves. The surface T of the central zones is equal to 83% of the surface of the transducer.

In the third configuration (bottom left of the figure), one of the central zones 52/54 or 56/58 of the transducer 50 are activated. The other zones are not activated and do not emit ultrasound waves. The surface T of the central zones is equal to 33% of the surface of the transducer.

In the fourth configuration (bottom right of the figure), of the central zones 52/54 or 56/58 of the transducer 50 are activated. The other zones are not activated and do not emit ultrasound waves. The surface T of the central zones is equal to 10% of the surface of the transducer.

It can be seen that most of the thermal dose is delivered along the emission axis or close to the emission axis unless only the central zones 52/54 or 56/58 are activated.

Moreover, the effect is more noticeable when the surface T of the central zones is equal to 33% of the total surface of the transducer.

When the surface T decreases (for example is equal to or lower than 10% of the total surface of the transducer) the pressure and the thermal dose delivered decrease off-axis and become uniform along the pathway between the transducer and the focal zone, this may need to increase the pressure for treating and thus this may lead to potential side effects in untargeted regions. As a corollary, when the surface T becomes closer to the total surface of the transducer (for example 83%) the pressure and so the thermal dose delivered off-axis decreases and increases along the acoustic axis, limiting the desired effect.

An advantage of the invention is that the transducer 6 can deliver the required pressure at a target location of the host material 20 that is not aligned with the emission axis without having to move or reposition the transducer. It is thus possible to target an increased volume within the host material 20 simply by activating different emission zones, without having to move or reposition the transducer relative to the host material 20, and more importantly without the need of a large number of elements (and therefore associated electronics) and a long processing time.

Figure 6:
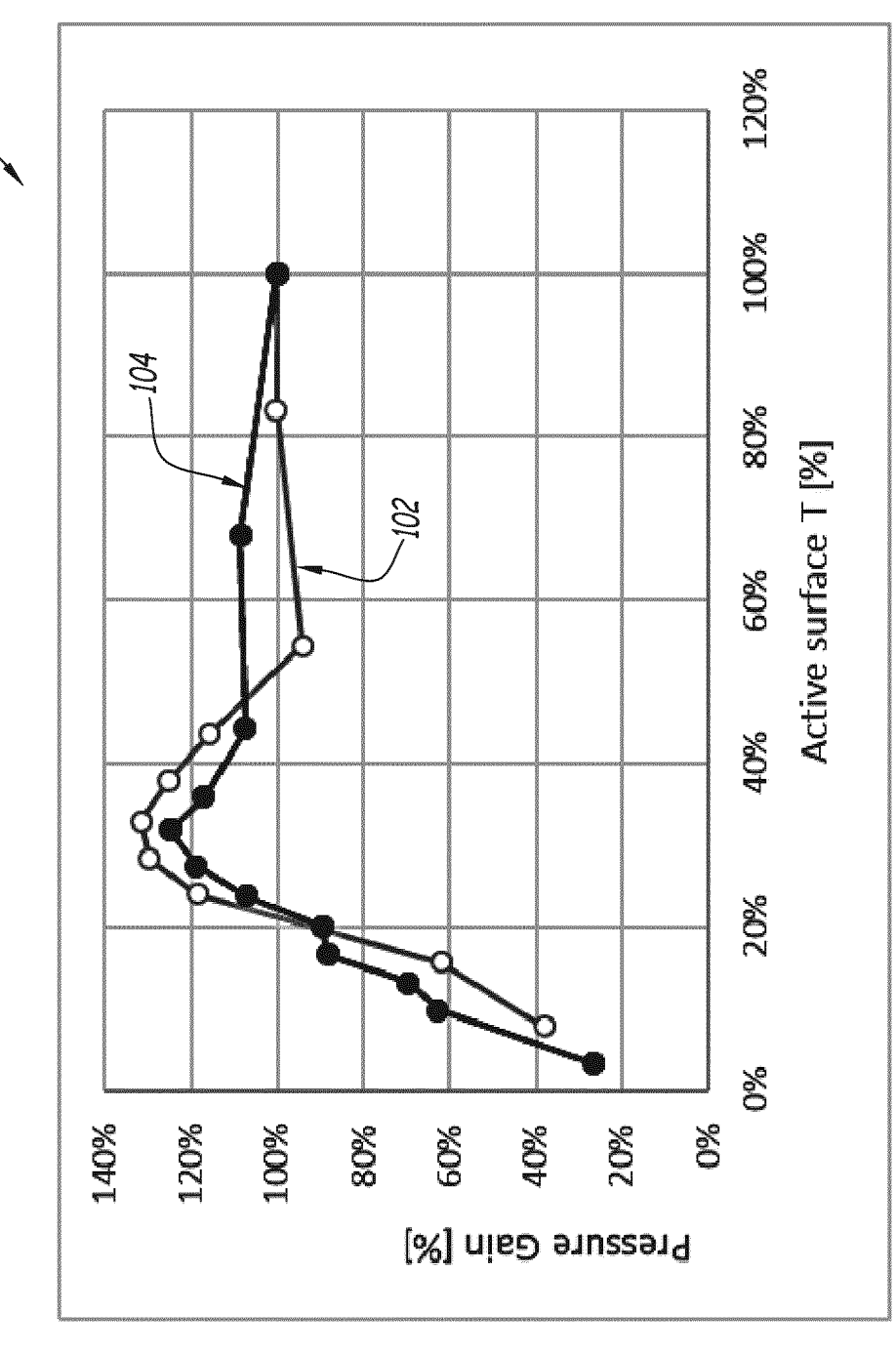
FIG. 6 illustrates a graph displaying a comparison of the relative gain in the pressure delivered by several ultrasonic transducers, as a function of the ratio between the surface of one of the rectilinear emitting zone and the total surface of said transducer.

On FIG. 6, the graph 100 illustrates a comparative example based on numerical simulations showing the evolution of the pressure gain for different values of the surface T (expressed as a ratio relative to the surface of the transducer) for two different transducers 6 (curves 102 and 104).

In this example, both the first transducer and the second transducer correspond to the transducer 50 illustrated in FIG. 2 insert (c) and FIG. 5, albeit with different dimensions. In both cases, the base portion of the transducer is a truncated cone, built on a portion of the interior envelope of a spindle torus.

The results given for the first transducer (curve 102) are the same as the results presented on FIG. 6 (curve 84). Dimensions and other characteristic features of the transducers are summarized in the table below.

| | Outer diameter (mm) | Inner diameter (mm) | Radius of curvature (mm) | Focal ring diameter (mm) | Working frequency (MHz) |
|---|---|---|---|---|---|
| First transducer (curve 102) | 120 | 45 | 130 | 20 | 1.1 |
| Second transducer (curve 104) | 150 | 42 | 120 | 10 | 1.5 |

The outer diameter and the inner diameter refer to dimensions of the base portion (the inner diameter corresponds to the diameter of the base portion at a lower end, and the outer diameter corresponds to the diameter of the base portion at an upper end, as visible on FIG. 5, the base portion being tapered open from the lower end towards the upper end.

The Radius of curvature is associated to the curvature of the walls of the base portion.

The data shows that improved pressure gain performances can be reached using a surface T comprised between 25% and 50% of the transducer surface, and especially for values of surface radio T of 33%.

Many other embodiments are possible.

In optional embodiments, the device 2 may be used on a human patient as part of a therapeutic method.

The embodiments and alternatives described above may be combined with each other in order to create new embodiments of the invention, within the scope of the claims.

The invention claimed is:

1. An ultrasonic transducer, comprising a base portion having a surface, the base portion displaying a rotational symmetry relative to the emission axis of the ultrasonic transducer, the emission axis being in a central position of the base portion, wherein said surface of the base portion is divided into several ultrasound emission zones, the several ultrasound emission zones having, collectively, a total area and comprising one or more central ultrasound emission zones and one or more other ultrasound emission zones, each of the one or more other ultrasound emission zones being adjacent to and separated by respective rectilinear cutout lines from at least one of the one or more central ultrasound emission zones, each of the one or more central ultrasound emission zones having a rectilinear band shape, being arranged centrally on said surface of the base portion, and being distributed on both sides of the emission axis of the ultrasonic transducer, and the one or more central ultrasound emission zones have respective areas that, collectively, comprise between 25% and 50% of the total area of the several ultrasound emission zones, and wherein the ultrasonic transducer comprises a layer of piezoelectric material and at least one electrically conductive electrode layer arranged in contact with the layer of piezoelectric material, wherein the electrode layer is divided in a plurality of contact pads, the association of each contact pad with the piezoelectric layer forming an ultrasound emitter element, wherein each emission zone of the electronic transducer comprises one or more of said contact pads;

wherein the ultrasonic transducer is configured so that the one or more other ultrasound emission zones can be activated independently from the one or more central ultrasound emission zones.

2. The ultrasonic transducer of claim 1, wherein a first central ultrasound emission zone and a second central ultrasound emission zone among the one or more central ultrasound emission zones of the ultrasonic transducer are arranged perpendicular relative to each other to form a cross shape.

3. The ultrasonic transducer according to claim 2, wherein the ultrasonic transducer is further configured so that the first central ultrasound emission zone and the second central ultrasound emission zone can be activated independently from each other.

4. The ultrasonic transducer according to claim 2, wherein the ultrasonic transducer is further configured so that the first central ultrasound emission zone and the second central ultrasound emission zone can have different widths and/or different lengths.

5. The ultrasonic transducer according to claim 2, wherein each of the first central ultrasound emission zone and the second central ultrasound emission zone can be divided into two parts that can be activated independently.

6. The ultrasonic transducer of claim 1, wherein a first central ultrasound emission zone and a second central ultrasound emission zone among the one or more central ultrasound emission zones of the ultrasonic transducer are arranged so as to cross each other with any angle between the first central ultrasound emission zone and second central ultrasound emission zone.

7. The ultrasonic transducer according to claim 1, wherein the ultrasonic transducer is configured so that each of the several ultrasound emission zones of the ultrasonic transducer can be activated independently from one another.

8. The ultrasonic transducer according to claim 1, wherein the base portion has a diameter that is between 10 mm and 300 mm.

9. The ultrasonic transducer according to claim 1, wherein the one or more central ultrasound emission zones have respective areas that, collectively, comprise 33% of the total area surface of the several ultrasound emission zones base portion.

10. The ultrasonic transducer according to claim 1, wherein the base portion has a concave shape.

11. The ultrasonic transducer according to claim 1, wherein the ultrasonic transducer is a high intensity focused ultrasound, HIFU, transducer.

12. The ultrasonic transducer according to claim 1, wherein the base portion has a diameter that is between 90 mm and 130 mm.

13. The ultrasonic transducer according to claim 10, wherein the base portion has a frustoconical shape or a toroidal shape.

14. A device comprising an ultrasonic transducer and a control unit connected to the ultrasonic transducer, wherein the ultrasonic transducer comprises a base portion having a surface, the base portion displaying a rotational symmetry relative to the emission axis of the ultrasonic transducer, the emission axis being in a central position of the base portion, wherein said surface is divided into several ultrasound emission zones, the several ultrasound emission zones having, collectively, a total area and comprising one or more central ultrasound emission zones and one or more other ultrasound emission zones, each of the one or more other ultrasound emission zones being adjacent to and separated by respective rectilinear cutout lines from at least one of the one or more central ultrasound emission zones, each of the one or more central ultrasound emission zones having a rectilinear band shape, being arranged centrally on said surface of the base portion, and being distributed on both sides of the emission axis of the ultrasonic transducer, and the one or more central ultrasound emission zones have respective areas that, collectively, comprise between 25% and 50% of the total area of the several ultrasound emission zones, wherein the ultrasonic transducer comprises a layer of piezoelectric material and at least one electrically conductive electrode layer arranged in contact with the layer of piezoelectric material, wherein the electrode layer is divided in a plurality of contact pads, the association of each contact pad with the piezoelectric layer forming an ultrasound emitter element, wherein each emission zone of the electronic transducer comprises one or more of said contact pads;

wherein the ultrasonic transducer is configured so that the one or more other ultrasound emission zones of the ultrasonic transducer can be activated independently from the one more central ultrasound emission zones, and wherein said control unit comprises at least one signal generator configured to generate electrical signals for driving the ultrasound emission zones.

15. The device of claim 14, wherein the control unit is further configured to activate each of the several ultrasound emission zones of the ultrasonic transducer independently from each other.

16. The device of claim 14, wherein the device is a therapeutic ultrasonic device configured to generate at least one focused ultrasound beam.

17. The device of claim 14 wherein said control unit further comprises a matching circuit between the signal generator and the several ultrasonic emission zones.

\* \* \* \* \*